United States Patent
Johannaber

(10) Patent No.: US 9,955,979 B2
(45) Date of Patent: May 1, 2018

(54) EXTRAMEDULLARY RESECTION GUIDE AND METHODS

(71) Applicant: Zimmer, Inc., Warsaw, IN (US)

(72) Inventor: Kenneth D Johannaber, Rancho Murieta, CA (US)

(73) Assignee: Zimmer, Inc., Warsaw, IN (US)

( * ) Notice: Subject to any disclaimer, the term of this patent is extended or adjusted under 35 U.S.C. 154(b) by 908 days.

(21) Appl. No.: 13/789,049

(22) Filed: Mar. 7, 2013

(65) Prior Publication Data

US 2014/0257307 A1    Sep. 11, 2014

(51) Int. Cl.
*A61B 17/17* (2006.01)
*A61B 17/15* (2006.01)
*A61B 90/13* (2016.01)

(52) U.S. Cl.
CPC ............ *A61B 17/155* (2013.01); *A61B 17/17* (2013.01); *A61B 17/1703* (2013.01); *A61B 17/1714* (2013.01); *A61B 17/1739* (2013.01); *A61B 17/1764* (2013.01); *A61B 90/13* (2016.02)

(58) Field of Classification Search
CPC ... A61B 17/155; A61B 17/1764; A61B 17/15; A61B 17/154; A61B 17/157; A61B 2019/202
USPC ..................................... 606/87–89
See application file for complete search history.

(56) References Cited

U.S. PATENT DOCUMENTS

| | | |
|---|---|---|
| 7,726,974 B2 | 6/2010 | Shah et al. |
| 8,021,368 B2 | 9/2011 | Haines |
| 8,436,521 B2 | 5/2013 | Shim |
| 2005/0021039 A1 | 1/2005 | Cusick et al. |
| 2005/0070897 A1 | 3/2005 | Petersen |
| 2006/0034091 A1 | 2/2006 | Kovacik |

(Continued)

FOREIGN PATENT DOCUMENTS

| | | | |
|---|---|---|---|
| EP | 1444957 A1 | 8/2004 | |
| EP | 1444957 A1 * | 11/2004 | ............. A61B 17/15 |

(Continued)

OTHER PUBLICATIONS

"International Application Serial No. PCT/US2014/018900, International Search Report mailed May 23, 2014", 5 gs.

(Continued)

*Primary Examiner* — Tatiana Nobrega
*Assistant Examiner* — Jessica Weiss
(74) *Attorney, Agent, or Firm* — Schwegman Lundberg & Woessner, P.A.

(57) ABSTRACT

A bone cut positioning system and associated method are disclosed. The bone cut positioning system can include a positioning assembly, including a femoral attachment member, including a tongue with at least one fixation aperture configured to be fixed to a distal end of a femur. The positioning assembly can further include a light emitter mounting member configured to receive a light emitter, a channel configured to receive a depth selector slide, and a varus-valgus adjustment member configured to adjust a position of the positioning assembly relative to the femur to achieve a desired varus-valgus angle. A flexion-extension adjustment member can be configured to adjust a flexion-extension position of the positioning assembly relative to a flexion-extension of a knee joint and a guide member can be configured to extend from the depth selector slide.

19 Claims, 10 Drawing Sheets

(56) References Cited

U.S. PATENT DOCUMENTS

| | | | |
|---|---|---|---|
| 2007/0043375 A1* | 2/2007 | Anissian | A61B 17/15 606/87 |
| 2007/0073306 A1 | 3/2007 | Lakin et al. | |
| 2007/0173851 A1 | 7/2007 | Mcmillen et al. | |
| 2008/0183178 A1 | 7/2008 | Collazo | |
| 2008/0195109 A1 | 8/2008 | Hunter et al. | |
| 2009/0234360 A1* | 9/2009 | Alexander | A61B 17/15 606/88 |
| 2009/0239393 A1 | 9/2009 | Shah | |
| 2010/0063508 A1 | 3/2010 | Borja et al. | |
| 2010/0198275 A1 | 8/2010 | Chana et al. | |
| 2011/0208093 A1* | 8/2011 | Gross | A61B 5/4528 600/587 |
| 2012/0245589 A1 | 9/2012 | Fisher et al. | |
| 2014/0257308 A1 | 9/2014 | Johannaber | |
| 2016/0305641 A1 | 10/2016 | Lin | |
| 2017/0100133 A1 | 4/2017 | Johannaber | |

FOREIGN PATENT DOCUMENTS

| | | |
|---|---|---|
| EP | 2964110 B1 | 12/2016 |
| WO | WO-2012176077 A1 | 12/2012 |
| WO | WO-2014137726 A1 | 9/2014 |
| WO | WO-2014138384 A1 | 9/2014 |

OTHER PUBLICATIONS

"International Application Serial No. PCT/US2014/018900, Written Opinion mailed May 23, 2014", 6 pgs.

"International Application Serial No. PCT/US2014/021164, International Search Report mailed May 13, 2014", 5 pgs.

"International Application Serial No. PCT/US2014/021164, Written Opinion mailed May 13, 2014", 5 pgs.

"U.S. Appl. No. 13/789,087, Non Final Office Action mailed Sep. 11, 2015", 11 pgs.

"U.S. Appl. No. 13/789,087, Response filed Dec. 11, 2015 to Non Final Office Action mailed Sep. 11, 2015", 10 pgs.

"International Application Serial No. PCT/US2014/018900, International Preliminary Report on Patentability mailed Sep. 17, 2015", 8 pgs.

"International Application Serial No. PCT/US2014/021164, International Preliminary Report on Patentability mailed Sep. 17, 2015", 7 pgs.

"U.S. Appl. No. 13/789,087 Response filed Dec. 22, 2016 to Non Final Office Action dated Dec. 1, 2016", 9 pgs.

"U.S. Appl. No. 13/789,087, Advisory Action dated Jun. 27, 2016", 3 pgs.

"U.S. Appl. No. 13/789,087, Final Office Action dated Mar. 24, 2016", 11 pgs.

"U.S. Appl. No. 13/789,087, Non Final Office Action dated Dec. 1, 2016", 8 pgs.

"U.S. Appl. No. 13/789,087, Response filed May 23, 2016 to Final Office Action dated Mar. 24, 2016", 17 pgs.

"U.S. Appl. No. 13/789,087, Response filed Jul. 25, 2016 to Advisory Action dated Jun. 27, 2016", 16 pgs.

"U.S. Appl. No. 15/388,609, Preliminary Amendment filed Dec. 28, 2016", 7 pgs.

"European Application Serial No. 14712819.3, Response filed May 9, 2016 to Communication pursuant to Rules 161(1) and 162 EPC dated Oct. 29, 2015", 12 pgs.

"European Application Serial No. 14712950.6, Communication Pursuant to Article 94(3) EPC dated Nov. 7, 2016", 5 pgs.

"U.S. Appl. No. 13/789,087, Non Final Office Action dated Apr. 20, 2017", 21 pgs.

"European Application Serial No. 14712950.6, Response filed Mar. 13, 2017 to Office Action dated Nov. 7, 2016", 9 pgs.

"U.S. Appl. No. 13/789,087, Examiner Interview Summary dated Jul. 25, 2017", 3 pgs.

"U.S. Appl. No. 13/789,087, Notice of Allowance dated Nov. 3, 2017", 13 pgs.

"U.S. Appl. No. 13/789,087, Response filed Jul. 20, 2017 to Non Final Office Action dated Apr. 20, 2017", 15 pgs.

"U.S. Appl. No. 15/388,609, Non Final Office Action dated Nov. 3, 2017", 17 pgs.

* cited by examiner

EXTRAMEDULLARY RESECTION GUIDE AND METHODS

TECHNICAL FIELD

The present disclosure relates to bone cut positioning systems, and more specifically, to femoral bone cut positioning systems.

BACKGROUND

Orthopedic procedures for the replacement of all, or a portion of, a patient's joint typically require resecting (cutting) or reshaping the ends of the bones forming the joint. For example, total knee arthroplasty ("TKA") procedures typically include cutting open the knee, displacing the patella, resecting bone from the distal end of the femur, resecting bone from the proximal end of the tibia to prepare the joint for prosthetic femoral and tibial implant components. Resecting the distal end of the femur often involves making one or more cuts including a planar distal cut. Resecting the proximal end of the tibia often involves making a planar proximal cut. In view of the foregoing surgical steps, TKA procedures are invasive, but typically effective.

TKA procedures can be complicated by the fact that a mechanical axis of the leg does not typically line up with the anatomic axis or intramedullary canal. The mechanical axis includes a line from the center of a proximal joint to a distal joint of a long bone (e.g., femur or tibia), such that the mechanical axis is straight as it is a direct path between joint centers. The intramedullary generally follows the curvature of the femur, such that it is not straight as compared to mechanical axis.

Cut guides can be used to guide a saw and achieve the proper angle and position of the cuts performed during a TKA. Cut guides can be in the form of a guide member having slots therein for receiving and guiding the saw. In use, the guide member can be positioned against the bone with the assistance of positioning or alignment equipment. The proper positioning of such guide members is crucial to forming well-positioned bone cuts for attachment of the prosthetic femoral and tibial implant components. For example, the tibial cut affects spacing, alignment and balance between the tibia and femur when the knee is in flexion, and alignment and balance between the tibia and femur when the knee is in extension, as well as all points of articulation between extension and flexion. Once properly positioned and aligned, the guide member can be secured to the bone using bone pins or other securement means. For example, the guide member can be slidably mounted to an alignment guide, which can be mounted at an angle relative to an extramedullary guide or intramedullary rod. For an extramedullary tibial resection, an extramedullary guide can be located relative to the patient's anatomy to provide proper alignment relative to the tibia, and a guide member can be positioned on the proximal end of the tibia. Similarly, in an intramedullary tibial resection, an intramedullary rod can be inserted into a pre-drilled hole in the intramedullary canal of the tibia to provide anatomic alignment with a cut guide positioned on the proximal end of the tibia. For preparation of the femoral resection, an intramedullary rod can be positioned such that it extends across the distal end of the femur, and the cut guide can be positioned on the proximal end of the femur. The cut guide can be slid toward or away (medially-laterally) from the tibia or femur until it is properly positioned against the surface of the bone. The cut guide can then be secured to the bone with pins. The cut guide can be connected to the alignment guide using a pin/hole connect mechanism.

SUMMARY

To better illustrate the bone cut positioning system and related methods disclosed herein, a non-limiting list of examples is provided here:

In Example 1, a bone cut positioning system can comprise a positioning assembly, including a femoral attachment member configured to be fixed to a distal end of a femur and having a first tongue with at least one fixation aperture, a light emitter mounting member configured to receive a light emitter, a channel, a varus-valgus adjustment member configured to adjust a position of the positioning assembly relative to the femur to achieve a desired varus-valgus angle, a flexion-extension adjustment member configured to adjust a flexion-extension position of the positioning assembly relative to a flexion-extension of a knee joint, and a guide member configured to extend from a depth selector slide, the depth selector slide configured to be received within the channel of the positioning assembly.

In Example 2, the bone cut positioning system of Example 1 is optionally configured such that the depth selector slide can be magnetically coupled to the channel.

In Example 3, the bone cut positioning system of any one or any combination of Examples 1-2 is optionally configured such that the positioning assembly is manufactured from at least one biocompatible material.

In Example 4, the bone cut positioning system of any one or any combination of Examples 1-3 is optionally configured such that the femoral attachment member includes a second tongue with at least one fixation aperture configured to receive a pin for securing the femoral attachment member to the distal end of the femur.

In Example 5, the bone cut positioning system of any one or any combination of Examples 1-4 is optionally configured such that the light emitter mounting member includes a light emitter receiving aperture configured to receive at least a portion of the light emitter.

In Example 6, the bone cut positioning system of any one or any combination of Examples 1-5 is optionally configured to include a magnetic interface for magnetically securing the light emitter to the light emitter mounting member.

In Example 7, the bone cut positioning system of any one or any combination of Examples 1-6 is optionally configured such that the light emitter is configured to magnetically power on when received by the light emitter mounting member.

In Example 8, the bone cut positioning system of any one or any combination of Examples 1-7 is optionally configured such that the light emitter includes a laser light emitter.

In Example 9, the bone cut positioning system of any one or any combination of Examples 1-8 is optionally configured such that the guide member is a single-use, disposable device.

In Example 10, the bone cut positioning system of any one or any combination of Examples 1-9 is optionally configured such that the positioning assembly is reusable.

In Example 11, the bone cut positioning system of any one or any combination of Examples 1-10 is optionally configured to include a flexion-extension indicator.

In Example 12, the bone cut positioning system of any one or any combination of Examples 1-11 is optionally configured such that the flexion-extension indicator includes a bubble level.

In Example 13, the bone cut positioning system of any one or any combination of Examples 1-12 is optionally configured such that at least one of the varus-valgus and flexion-extension adjustment members is configured to receive an adjustment device.

In Example 14, the bone cut positioning system of any one or any combination of Examples 1-13 is optionally configured such that the first tongue is configured to provide a reference on at least one of a medial and lateral side on an anterior cortex of the femur.

In Example 15, a method for positioning a bone cut guide on a femur can comprise coupling a positioning assembly to a femur. The positioning assembly can include a femoral attachment member, including a tongue with at least one fixation aperture configured to receive a pin, a light emitter mounting member configured to receive a light emitter, a channel, a varus-valgus adjustment member configured to adjust a position of the positioning assembly relative to the femur to achieve a desired varus-valgus angle, and a flexion-extension adjustment member configured to adjust a flexion-extension position of the positioning assembly relative to a flexion-extension of a knee joint. The method can further include inserting a depth selector slide of a guide member into the channel, attaching the light emitter to the light emitter mounting member, wherein the light emitter indicates a varus-valgus angle of the femur, aligning the guide member relative to a distal end surface of the femur, coupling the guide member to the femur with at least one guide pin, removing the positioning assembly and the guide member from the femur, and sliding the bone cut guide over the at least one guide pin.

In Example 16, the method of Example 15 is optionally configured to further include adjusting the varus-valgus adjustment member to align a position of the positioning assembly with the indicated varus-valgus angle of the femur.

In Example 17, the method of any one or any combination of Examples 15-16 is optionally configure to further include adjusting the flexion-extension adjustment member to align a position of the positioning assembly with a flexion-extension angle of the knee joint.

In Example 18, the method of any one or any combination of Examples 15-17 is optionally configured such that the method is performed on a leg in full extension.

In Example 19, the method of any one or any combination of Examples 15-18 is optionally configured to further include adjusting the depth selector slide to a desired resection level.

In Example 20, a bone cut positioning system can comprise a positioning assembly including a femoral attachment member configured to be coupled to a distal end of a femur, the femoral attachment member including a first tongue portion having at least one fixation aperture configured to receive a fastening member and a second tongue portion having at least one fixation aperture configured to receive a fastening member. The positioning assembly can further include a light emitter mounting member configured to receive a light emitter, a channel, a magnetic interface disposed within the channel, a varus-valgus adjustment member configured to adjust a position of the positioning assembly relative to the femur to achieve a desired varus-valgus angle, and a flexion-extension adjustment member configured to adjust a flexion-extension position of the positioning assembly relative to a flexion-extension of a knee joint. The bone cut positioning system can further include a guide member extending from a depth selector slide, where the depth selector slide is configured to be received within the channel of the positioning assembly and secured within the channel by the magnetic interface.

In Example 21, the bone cut positioning system or method of any one or any combination of Examples 1-20 is optionally configured such that all elements or options recited are available to use or select from.

These and other examples and features of the present disclosure can provide the benefit of reducing errors that can occur from intramedullary techniques, such as an error in varus-valgus alignment. That is, the present disclosure can provide a more accurate extramedullary technique. Further benefits of the present disclosure can include a system or method of resecting a femur such that the amount of bone cut from the femur is substantially minimized. Benefits of the present disclosure can also include providing a resected fixation surface that provides an improved or more secure fit for TKA prosthetics, as compared to previous approaches. Further, the present disclosure can provide a system and method for use in a TKA or partial knee replacement procedure while a leg is in extension. Benefits of such examples can include providing a better overall alignment analysis for a surgeon. Further, the system can include a more stable femoral attachment member better suited for procedures on a leg in extension. In addition, the present disclosure can provide an extramedullary system or method that is less invasive than an intramedullary technique, thereby reducing potential for infection and recovery time for a patient. Further, because the examples of the present disclosure provide extramedullary techniques that do not require intramedullary rod insertion, risk of systemic embolism is substantially reduced. Examples described in the present disclosure can be used when extra-articular deformities exist or when existing hardware, such as an extended hip stem, makes an intramedullary technique difficult.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present disclosure describes a bone cut positioning system and related method of use. The bone cut positioning system and methods can be used in various examples to enhance or facilitate a total knee arthroplasty (TKA) procedure, a partial knee arthroplasty procedure, or any other suitable knee surgery procedure in which one or more cuts are made on a femur, such as a distal end of the femur. Generally, the examples described herein provide a means for positioning a bone cut on a femur. Although the following description focuses on TKA procedures, the described examples can also be used for partial knee arthroplasty procedures or other knee procedures in which femoral bone cuts are made.

Figure 1:
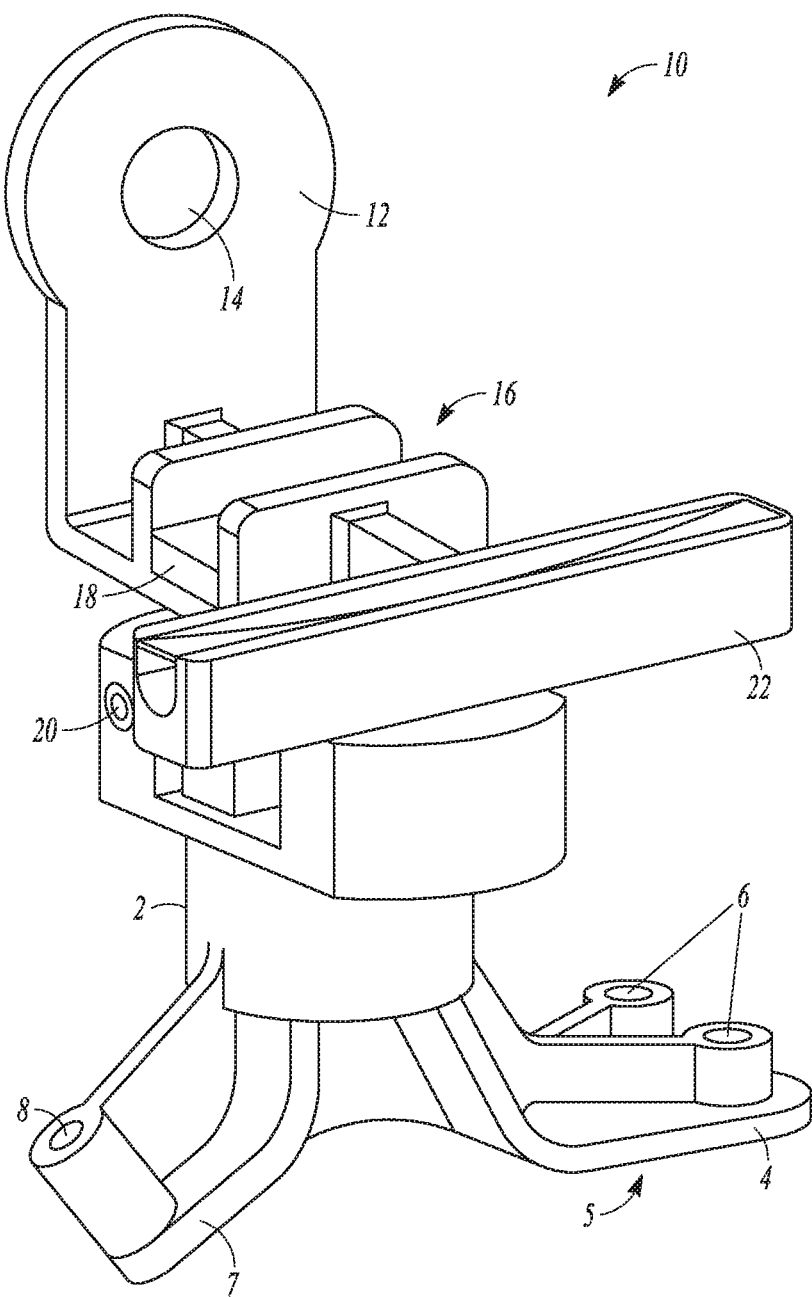
FIG. 1 is a perspective view of a positioning assembly, in accordance with at least one example.

FIG. 1 is a perspective view of a positioning assembly 10 in accordance with the present disclosure. One or more of the components of the positioning assembly 10 can be made of a biocompatible material, such as a material that does not produce a toxic, injurious, or immunological response in living tissue. Biocompatible materials can include, but are not limited to, ceramics, synthetic polymeric materials, and metallic materials such as titanium, a titanium alloy, cobalt chromium, cobalt chromium molybdenum, tantalum, or a tantalum alloy. In various examples, the positioning assembly 10 can be made of stainless steel. In various examples, the positioning assembly 10 can be reusable, such as after sterilization.

As illustrated in FIG. 1, the positioning assembly 10 can include a femoral attachment member 2 configured to be fixed to a distal end of a femur, a light emitter mounting member 12, a channel 16 configured to receive a depth selector slide, and a varus-valgus adjustment member 20.

The femoral attachment member 2 can include a first tongue 4 with at least one fixation aperture 6 configured to receive a pin or other fastening member. In various examples, the first tongue 4 can be configured such that it provides a reference on a medial or lateral side on an anterior cortex of the femur, when secured to the femur. The reference provided by the first tongue 4 can also be a flexion-extension axis reference. The first tongue 4 can include a substantially flat surface 5 configured to be secured to the anterior cortex of the femur. As illustrated in FIG. 1, the femoral attachment member 2 can include a second tongue 7 with at least one fixation aperture 8 configured to receive a pin or other fastening member for securing the femoral attachment member 2 to the distal end of the femur. In an example, the at least one fixation aperture can be oriented and positioned such that it provides a fixation point into the distal trochlea of the femur. The at least one fixation aperture 8 and corresponding pin or fastening member can be configured to provide stability to the positioning assembly 10 such that an intramedullary rod is not necessary, therefor decreasing invasiveness of the procedure.

The light emitter mounting member 12 can be configured to receive one or more light emitters. As illustrated in FIG. 1, the light emitter mounting member 12 can include a light emitter receiving hole 14 configured to receive at least a portion of a light emitter. The light emitter mounting member 14 can be disposed at any suitable position, such as above the femoral attachment member 2 when the femoral attachment member 2 is secured to the distal end of the femur. In an example, the light emitter mounting member 14 is configured such that the light emitter, when mounted, is substantially centered medially and laterally on the femur and perpendicular to a cutting plane, as described herein.

As described above, the channel 16 can be configured to receive a depth selector slide. In an example, the channel 16 can include a magnetic interface 18 configured for magnetically securing the light emitter to the light emitter mounting member 12. That is, in various examples, the depth selector slide, as described herein, can be magnetically coupled to the channel 16. A guide member can also be provided that is configured to extend from the depth selector slide, as described in further detail below.

The varus-valgus adjustment member 20 can be configured to adjust a position of the positioning assembly 10 relative to the femur to achieve a desired varus-valgus angle. In an example, the varus-valgus adjustment member 20 can be a screw that is configured to receive an adjustment device. For example, an adjustment device can include a screw driver, an Allen wrench, or any other suitable device that is capable of turning the varus-valgus adjustment member 20. The positioning assembly 10 can further include a flexion-extension indicator 22 configured to indicate an angle of a knee joint. Additional details of the structure and operation of the varus-valgus adjustment member 20 are described below in connection with FIGS. 4A and 4B.

Figure 2:
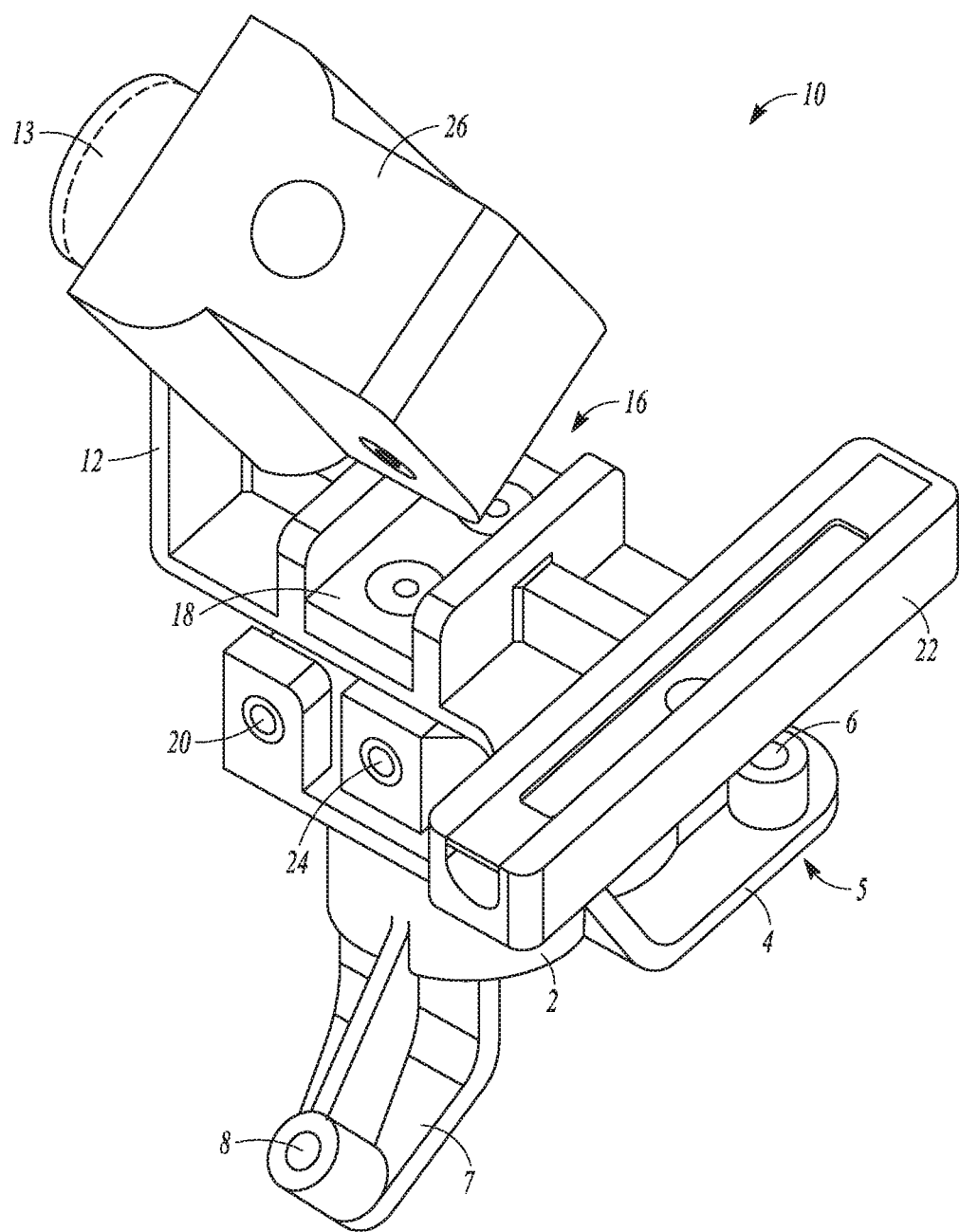
FIG. 2 is a perspective view of the positioning assembly and an attached light emitter, in accordance with at least one example.

FIG. 2 is an alternate perspective view of the positioning assembly 10 including a light emitter 26. In various examples, the light emitter 26 can be movable by a user, such that it can tilt relative to the positioning assembly 10. The light emitter 26 can generally include a light source configured to emit a light beam, as described herein. A light source can include, for example, a light emitting diode, a laser, or a combination thereof. In various examples, the light emitter 26 can emit a light beam in more than one direction, such as longitudinally along at least a portion of the femur and the tibia. The light emitter 26 can include a light emitter protrusion 13 configured to be received by light emitter receiving hole 14 (see FIG. 1) of the light emitter mounting member 12. The engagement between the light emitter 26 and the light emitter mounting member 12 can be configured to allow tilting of the light emitter 26 by the user to allow adjustment of the light beam along the femur and/or the tibia. Although the light emitter receiving hole 14 is shown as cylindrical in FIG. 1, it can be any three-dimensional geometric shape capable receiving the light emitter protrusion 13. Thus, the light emitter receiving hole 14 and the light emitter protrusion 13 can be defined by a similar three-dimensional shape, or non-similar three-dimensional shapes that allow for engagement between the light emitter protrusion 13 and the light emitter receiving hole 14. Alternatively, the light emitter 26 can be fixed, such as an integral assembly, with the positioning assembly 10.

The light emitter 26 can be configured to emit a light upon being coupled to the light emitter mounting member 12. For example, the lighter emitter 26 can include a magnetic switch that activates or powers on the light source upon being coupled to the light emitter mounting member 12. Alternatively or in addition, the light emitter 26 can include a manual on/off switch. For example, the light emitter 26 can include a switch that can be activated when exposed to the magnetic force of the light emitter mounting member 12. Additionally or alternatively, the light emitter can include a switch operable by a user to activate the light source.

As further illustrated in FIG. 2, the positioning assembly 10 can include a flexion-extension adjustment member 24. The flexion-extension adjustment member 24 can be configured to adjust the positioning assembly 10 to achieve a desired flexion-extension of a knee joint, as described herein.

Figure 3:
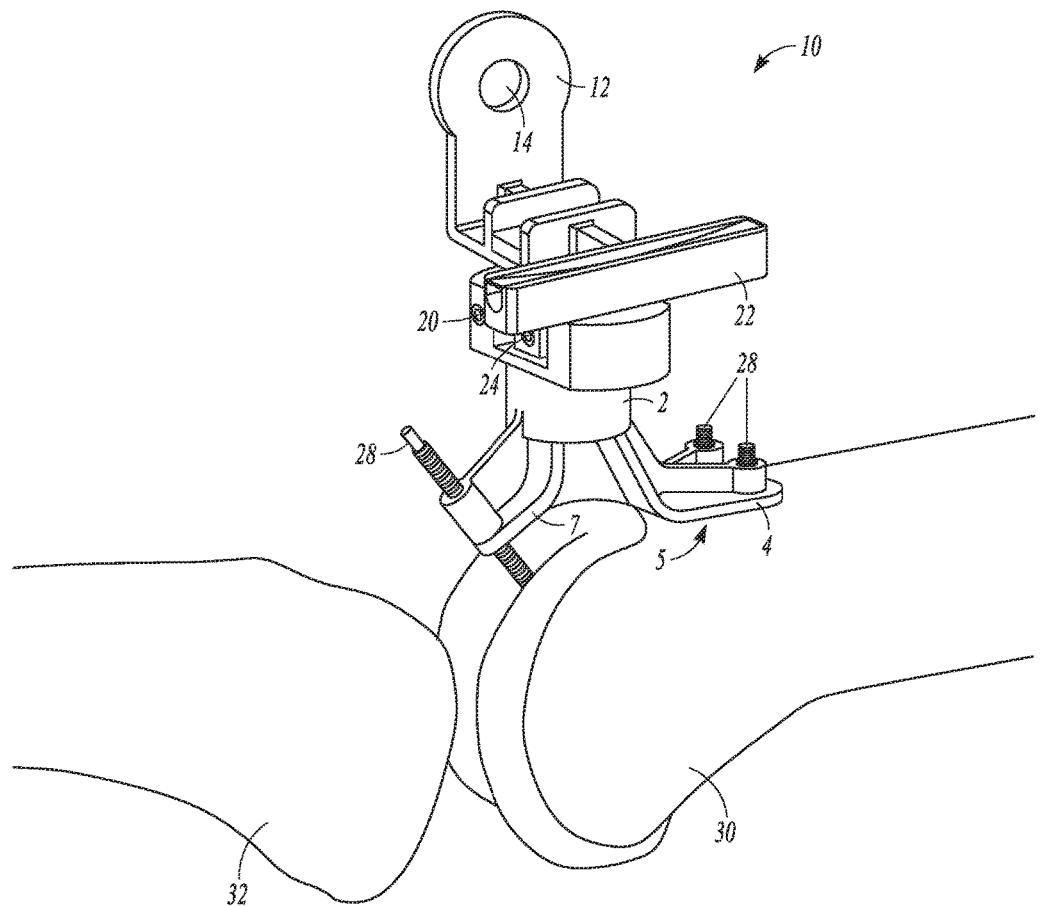
FIG. 3 is a perspective view of the positioning assembly engaged with a femur, in accordance with at least one example.

FIG. 3 is a perspective view of the positioning assembly 10 engaged with a femur 30. As shown, a pin 28 inserted into the distal trochlea of the femur 30 can provide stability for the positioning assembly 10. Pins 28 can also be positioned within the fixation apertures 6 of the first tongue 4 to secure the femoral attachment member 2 to the femur 30.

Figure 4A:
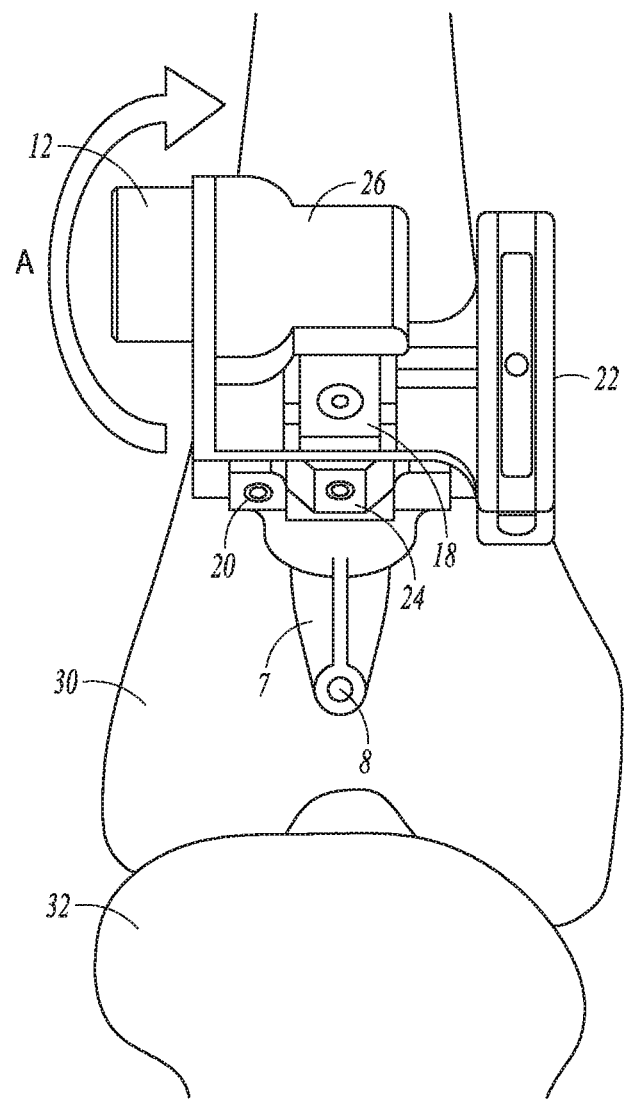
FIG. 4A is a top view of the positioning assembly and the lighter emitter engaged with the femur, in accordance with at least one example.

FIG. 4A is an alternate perspective view of the positioning assembly 10 engaged with the femur 30. With reference to FIG. 4A, the varus-valgus adjustment member 20 can adjust a position of the positioning assembly 10 relative to a varus-valgus angle or line of the femur 30 or the tibia 32. The varus-valgus adjustment member 20 can be operable to adjust a position of the light emitter mounting member 12 without adjusting a position of the femoral attachment member 2. Thus, adjusting the varus-valgus adjustment member 20 can rotate one or more components of the positioning assembly 10 in a direction A. In an example, the varus-valgus adjustment member 20 can be configured to rotate the light emitter mounting member 12 or light emitter 26 clockwise or counter clockwise relative to the femoral attachment member 2.

Figure 4B:
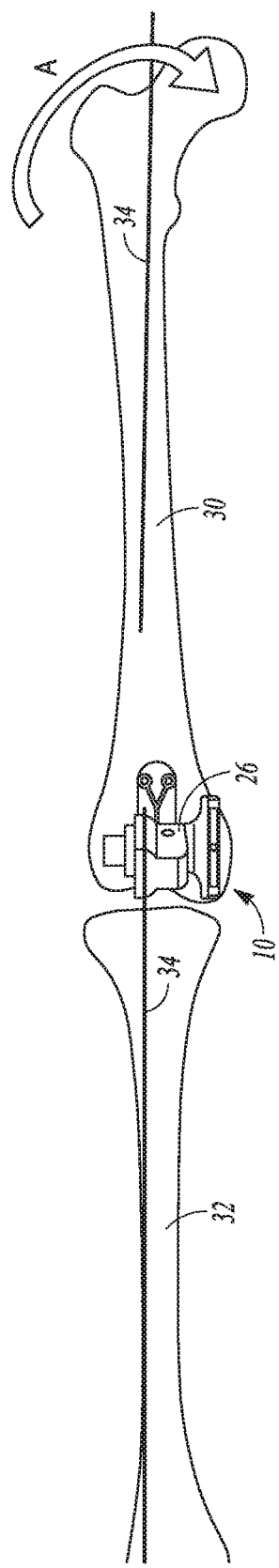
FIG. 4B is an alternative top view of the positioning assembly and the light emitter engaged with the femur, in accordance with at least one example.

As shown in FIG. 4B, the light emitter 26 can extend the light beam 34 longitudinally along at least a portion of the femur 30, the tibia 32, or both the femur 30 and the tibia 32. More specifically, the light emitter 26 can direct the light beam 34 toward a surface of the femur 30 or the tibia 32 for guiding orientation or adjustment of the positioning assembly 10. In various examples, the beam of light 34 can include a plane, a fan, a cross, or any other suitable light configuration. When the varus-valgus adjustment member 20 is adjusted, the beam of light 34 can be adjusted in the same direction A as the positioning assembly 10 or the light emitter mounting member 12, when the position of the light emitter mounting member 12 is adjusted independently of and relative to the femoral attachment member 2. The light beam 34 can be adjusted in the direction A until a desired varus-valgus alignment between the varus-valgus line of the femur 30 and/or tibia 32 and the positioning assembly 10 is achieved.

Figure 5:
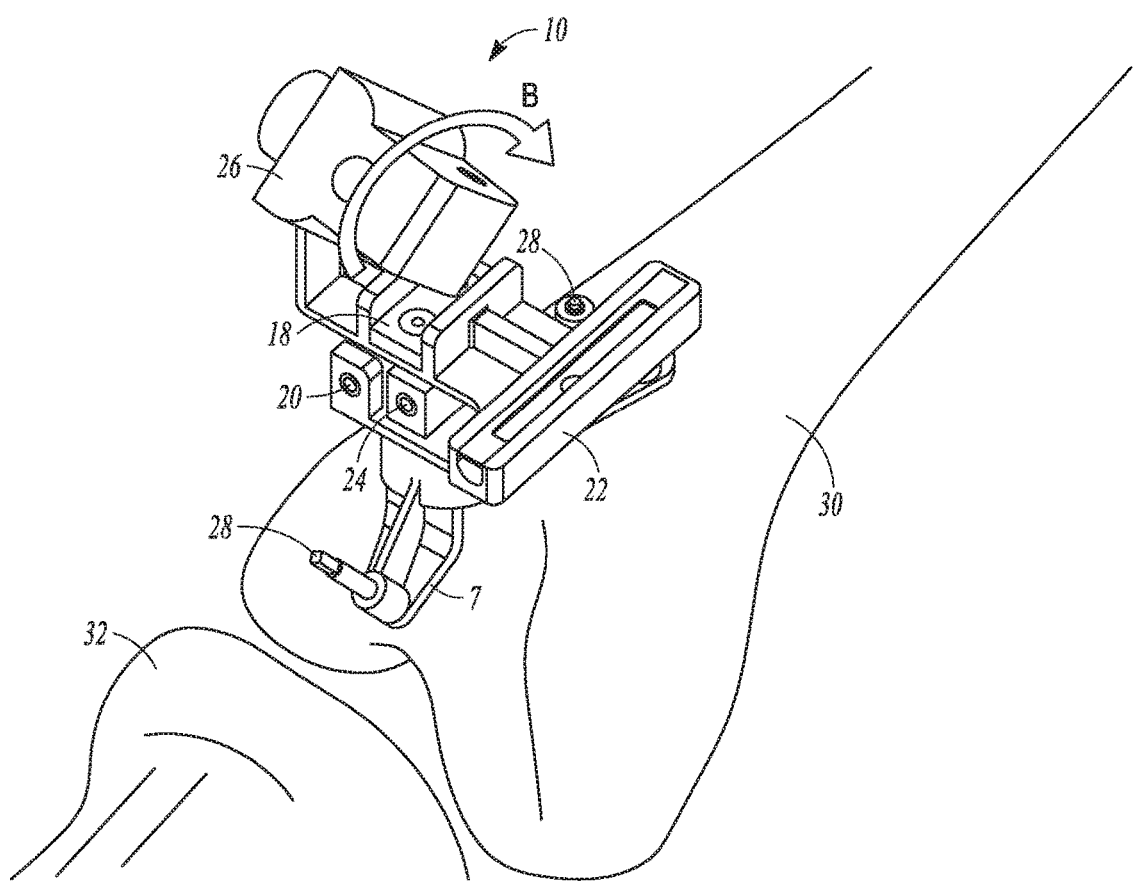
FIG. 5 is an alternative perspective view of the bone cut positioning system and the light emitter engaged with the femur, in accordance with at least one example.

FIG. 5 illustrates another perspective view of the positioning assembly 10 mounted on the femur 30. With reference to FIG. 5, the flexion-extension adjustment member 24 can adjust the positioning assembly 10 in a direction B. The flexion-extension indicator 22 can indicate a desired flexion-extension alignment of the positioning assembly 10 as selected by a user through adjustment of the flexion-extension adjustment member 24. The flexion-extension indicator 22 can include any suitable type of level indicator, such as a ball level indicator, a bubble level indicator, or a digital inclinometer. In operation, the user can manipulate the flexion-extension adjustment member 24 until a desired flexion-extension angle has been achieved as visually displayed by the flexion-extension indicator 22. In various examples, the desired flexion-extension angle can be between 0 degrees and about 5 degrees flexion, although other ranges are also contemplated. The flexion-extension adjustment member 24 can be adjusted when the leg is in full-extension, such as when compression is applied to the leg, or when the leg is in partial flexion.

Figure 6:
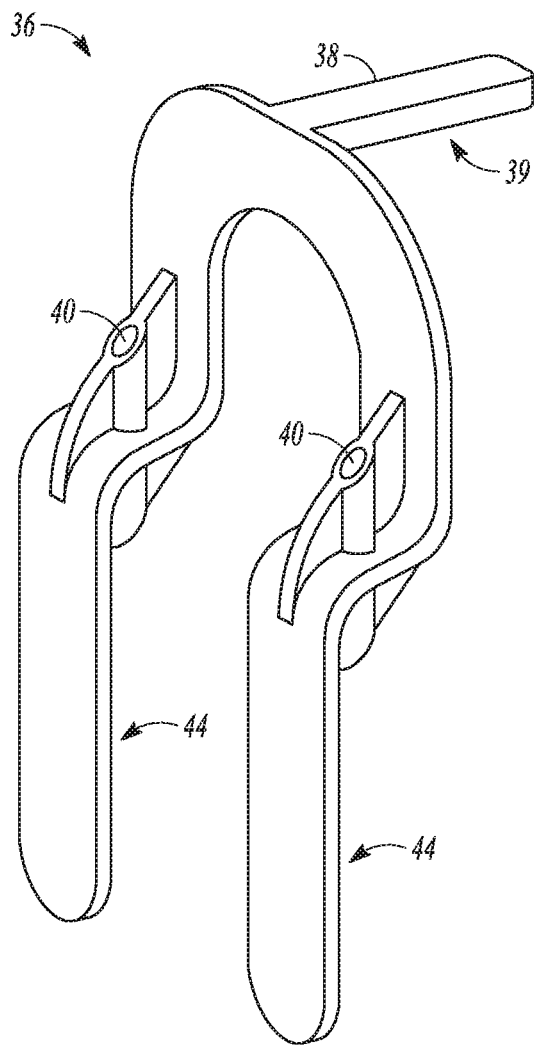
FIG. 6 is a perspective view of a guide member, in accordance with at least one example.

FIG. 6 is a perspective view of a guide member 36, such as a pin guide. As illustrated in FIG. 6, the guide member 36 can include a depth selector slide 38. The depth selector slide 38 can include a magnetic interface 39 configured to magnetically interact with the magnetic interface 18 (see FIG. 1) of the channel 16 (see FIG. 1). The depth selector slide magnetic interface 39 can be configured to contact or be positioned sufficiently close to the magnetic interface 18 of the channel 16 such that the depth selector slide 38 can be retained within the channel 16. The magnetic force between the magnetic interface 39 of the depth selector slide 38 and the magnetic interface 18 of the channel 16 can be strong enough to temporarily fix the depth selector slide 38 within the channel 16, but weak enough such that a user can reposition remove the depth selector slide 38 from the positioning assembly 10 by pushing, pulling, or lifting the depth selector slide 38. In various examples, the guide member 36 can include one or more apertures 40 configured to receive a pin or other fastening member for securing the guide member 36 to the femur.

The guide member 36 can include a femoral contact surface 44 configured to contact a surface of the distal femur, such as a condyle of the femur. In an example, the femoral contact surface 44 can be configured to contact a high point of the distal femur such that a resection depth between about 1 mm and about 20 mm can be determined. After making contact with the desired portion of the femur, the guide member 36 can be secured to the femur by inserting one or more pins or other fastening members through the one or more apertures 40.

Figure 7:
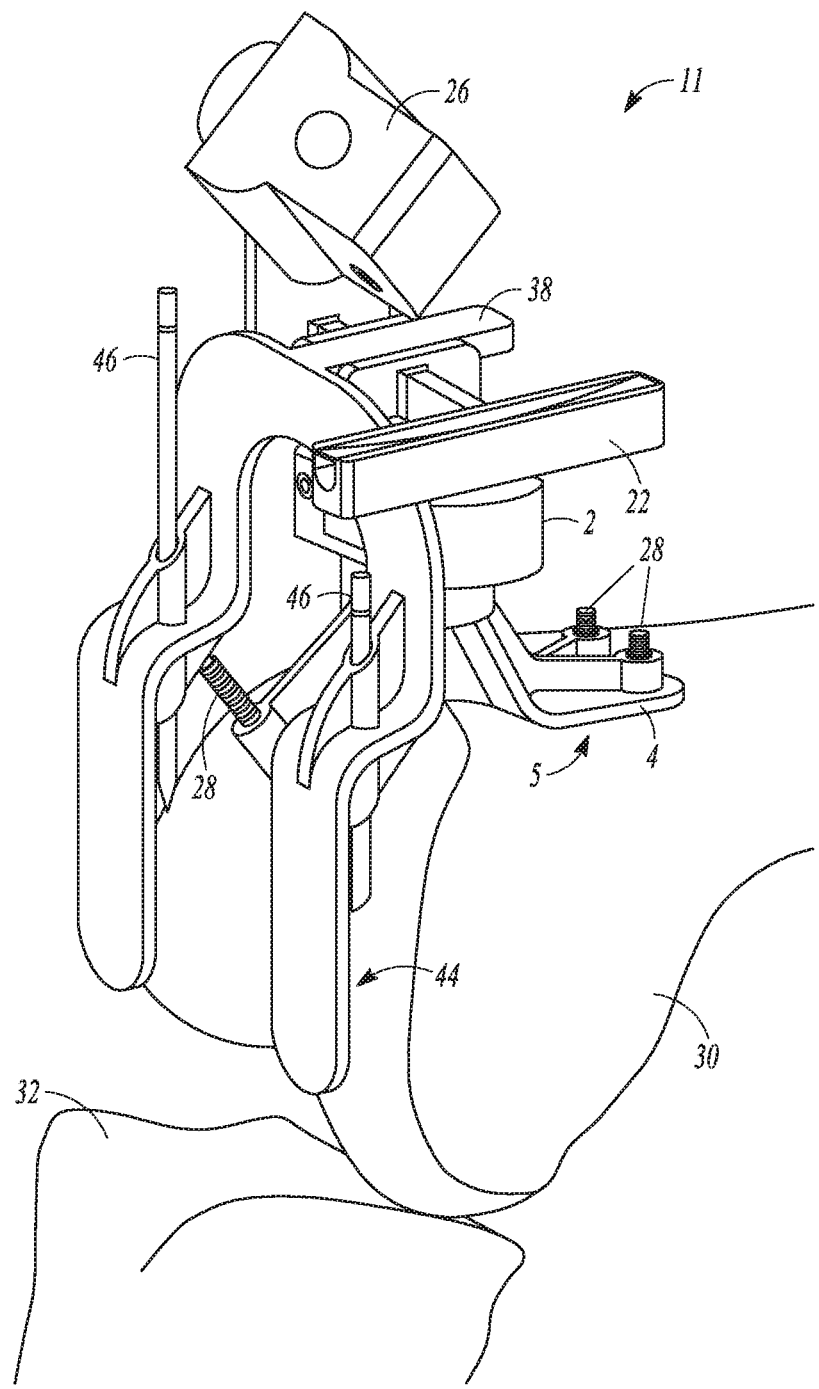
FIG. 7 is a perspective view of the positioning assembly and the guide member, which together form a bone cut positioning system, in accordance with at least one example.

FIG. 7 is a perspective view of the guide member 36 coupled to the positioning assembly 10, which together form a bone cut positioning system 11. As discussed above with reference to FIG. 3, pins 28 can be inserted through the first tongue 4 and the second tongue 7 to secure the femoral attachment member 2 to the femur 30. As illustrated in FIG. 7, pins 46 can also be inserted through the apertures 40 in the guide member 36 to secure the guide member 36 to the femur 30.

Figure 8:
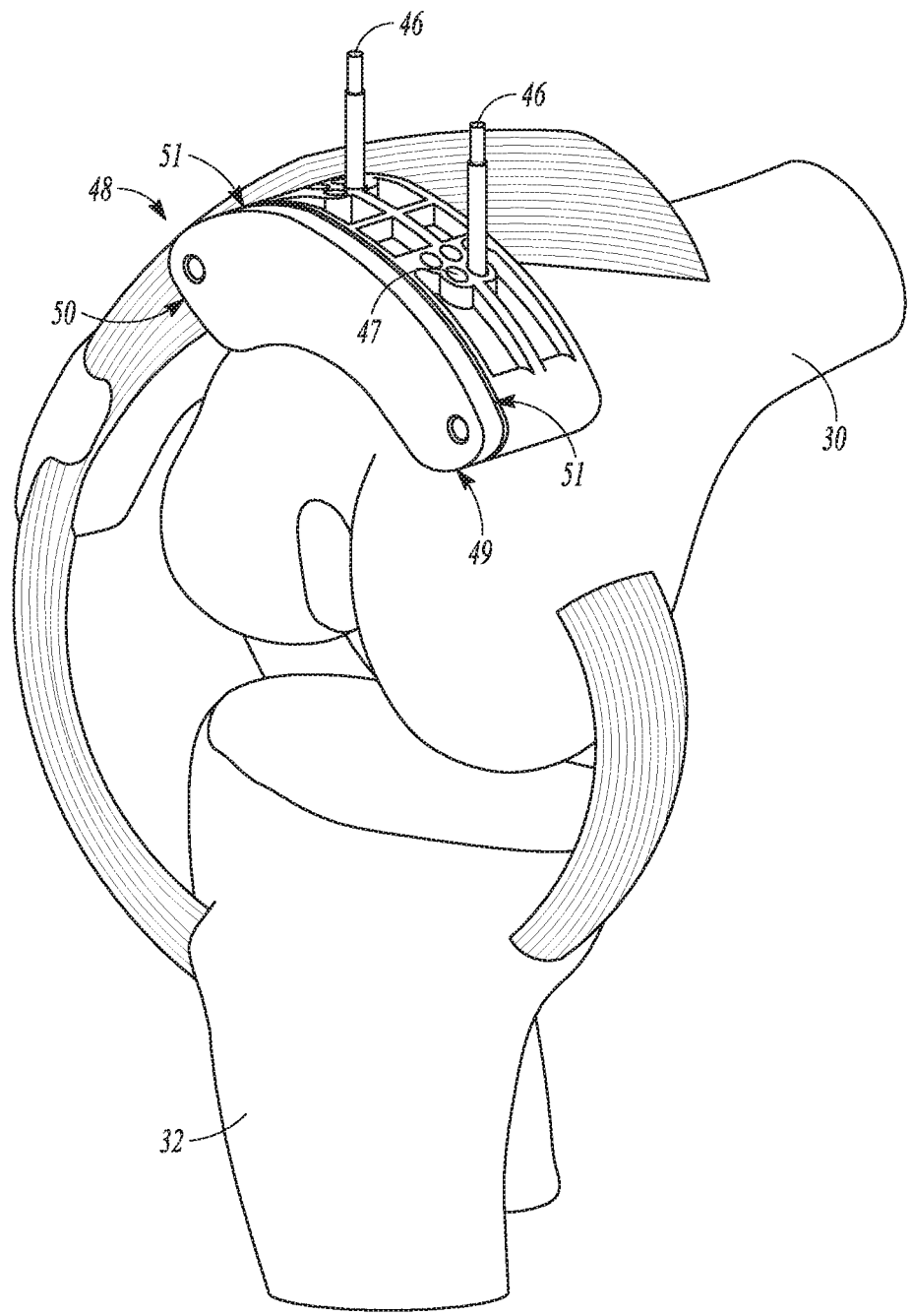
FIG. 8 is a perspective view of a cut guide engaged with the femur, in accordance with at least one example.

FIG. 8 is a perspective view of a cut guide 48 mounted on the femur 30 after the bone cut positioning system 11 has been removed from the femur 30. In the example previously described, the bone cut positioning system 11 can be decoupled from the femur 30 by removing the pins 28. After removing the pins 28 the bone cut positioning system 10 can be slid off the femur 30 leaving only the pins 46 engaged with the femur 30. The cut guide 48 can be slid over the pins 46 by inserting the pins 46 within one or more apertures 47 formed in the cut guide 48. The cut guide 48 can include one or more cutting surfaces 50, one or more cutting slots 51, or a combination of such elements. With reference to FIG. 8, the cutting surface 50 and the cutting slots 51 can be configured for guiding a saw or other cutting instrument. In an example, at least one of the cutting surface 50 and the cutting slots 52 can be oriented along a plane that is substantially perpendicular to the light beam 34 of FIG. 4B.

The cut guide 48 can be a single-use, disposable device manufactured from a biocompatible material, as described herein. As illustrated in FIG. 8, at least a portion of the biocompatible material forming the cut guide 48 can be a resorbable material, such as a portion 49 of the cut guide 48 that includes the cutting surface 50 and the cutting slots 51. A resorbable material can include a material capable of being absorbed into tissue of a human subject upon separation of the material from the guide member 48. For example, the resorbable material can include a poly-L-lactide, a poly-D-lactide, a poly-DL-lactide, a ployglycolide, a polycaprolactone, or a combination thereof. In an example, the resorbable material portion 49 of the cut guide 48 can be removable or replaceable, such that the guide member 48 can be reused after sterilization and replacement of the portion 49.

Figure 9:
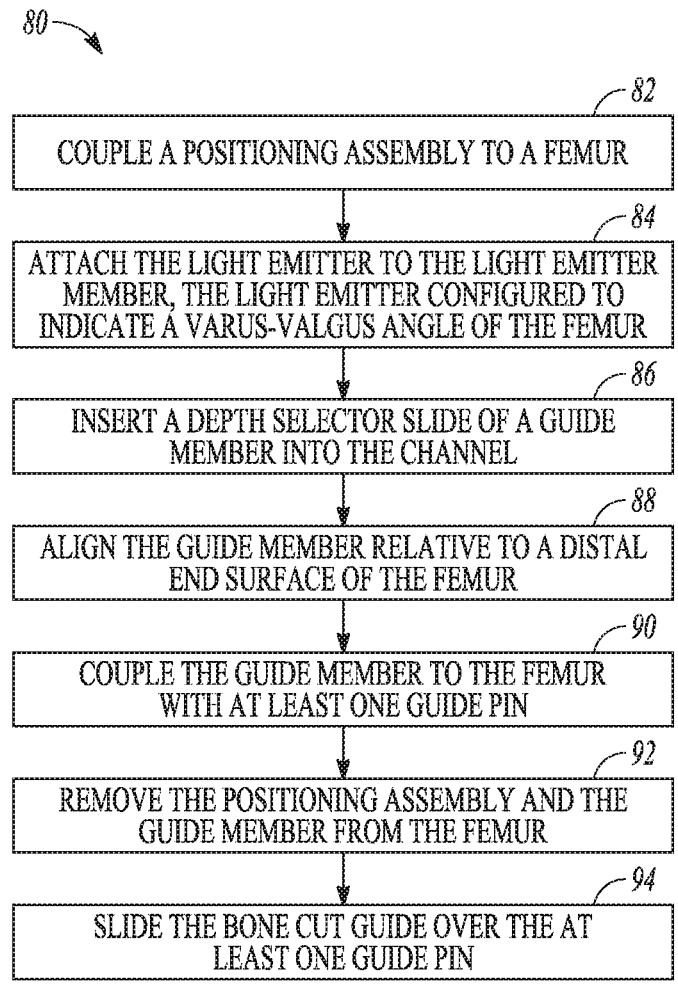
FIG. 9 is a method for positioning a cut guide on a femur, in accordance with at least one example.

FIG. 9 is a method 80 for positioning a bone cut guide on a femur. The method 80 can include coupling 82 a positioning assembly to a femur, including inserting at least one pin or other fastening member into a distal trochlea of the femur. The positioning assembly can include a femoral attachment member including a tongue with at least one fixation aperture configured to receive a pin or other fastening member, a light emitter mounting member configured to receive a light emitter, a channel configured to receive a depth selector slide, a varus-valgus adjustment member configured to adjust a position of the positioning assembly relative to the femur to achieve a desired varus-valgus angle, a flexion-extension adjustment member configured to adjust a flexion-extension position of the positioning assembly relative to a flexion-extension of a knee joint, and a guide member configured to extend from the depth selector slide.

The method 80 can further include attaching 84 the light emitter to the light emitter mounting member. Attaching the light emitter to the light emitter mounting member can further include activating a light source, such as magnetically or by an on/off switch. Upon activation, the light emitter can be configured to indicate a varus-valgus angle of the femur.

In various examples, the method 80 can include sliding 86 a guide member, extending from the depth selector slide, into the channel of the positioning assembly. A magnetic interface can be formed between the channel and the depth selector slide, as described herein. The method 80 can include aligning 88 the guide member relative to a high point of a distal end of the femur, including touching a contact surface of the guide member with a high point of the distal femur, as described herein. Aligning 88 can further include adjusting the depth selector slide to a desired resection level.

The method 80 can further include coupling 90 the guide member to the femur with at least one guide pin or other fastening member. Further, the method 80 can include removing 92 the positioning assembly and the guide member from the femur, and sliding 94 a cut guide over the at least one guide pin.

In various examples, the method 80 can further include adjusting the varus-valgus adjustment member to align the positioning assembly with a desired varus-valgus angle of the femur, such as prior to mounting the guide member. For example, a light beam emitted by the light emitter can be aligned with a varus-valgus line of the femur and/or tibia. Further, the method can include adjusting the flexion-extension adjustment member to align the positioning assembly with a flexion-extension angle of the knee joint. Adjusting the flexion-extension adjustment member can include adjusting the flexion-extension member until a flexion-extension indicator indicates the positioning assembly is substantially level. The method 80 can be performed on the leg in full extension, such as with applied compression, or when the leg is in partial flexion.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other examples can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The invention claimed is:

1. A bone cut positioning system, comprising:
   a positioning assembly, including:
      a femoral attachment member including a base portion and a first tongue with at least one fixation aperture, the first tongue extending away from the base portion and configured to be attached to the anterior cortex of a femur, thereby providing a flexion-extension axis reference;
      a light emitter mounting member configured to receive a light emitter;
      a channel;
      a varus-valgus adjustment member configured to adjust a position of the positioning assembly relative to the femur to achieve a desired varus-valgus angle; and
      a flexion-extension adjustment member configured to adjust a flexion-extension position of the positioning assembly; and
   a guide member configured to extend from a depth selector slide, the depth selector slide configured to be received within the channel of the positioning assembly, the guide member comprising at least one femoral contact surface, the depth selector slide configured to move within the channel to move the guide member proximally-distally relative to the femur to cause the at least one femoral contact surface to engage the distal end of the femur to set a desired resection level.

2. The bone cut positioning system of claim 1, wherein the depth selector slide is configured to be magnetically coupled to the channel.

3. The bone cut positioning system of claim 1, wherein the positioning assembly is manufactured from at least one biocompatible material.

4. The bone cut positioning system of claim 1, wherein the femoral attachment member includes a second tongue with at least one fixation aperture configured to receive a pin for securing the femoral attachment member to the anterior cortex of the femur proximal to the distal end of the femur.

5. The bone cut positioning system of claim 1, wherein the light emitter includes a laser light emitter.

6. The bone cut positioning system of claim 1, wherein the guide member is a single-use, disposable device.

7. The bone cut positioning system of claim 1, wherein the positioning assembly is reusable.

8. The bone cut positioning system of claim 1, further including a flexion-extension indicator.

9. The bone cut positioning system of claim 8, wherein the flexion-extension indicator includes a bubble level.

10. The bone cut positioning system of claim 1, wherein at least one of the varus-valgus and flexion-extension adjustment members is configured to receive an adjustment device.

11. The bone cut positioning system of claim 1, wherein the first tongue is further configured to provide a reference on at least one of a medial and lateral side on the anterior cortex of the femur.

12. The bone cut positioning system of claim 1, wherein at least a portion of the base portion of the femoral attachment member is cylindrical.

13. A bone cut positioning system, comprising:
a positioning assembly, including:
a femoral attachment member configured to be fixed to a distal end of a femur, the femoral attachment member including a first tongue with at least one fixation aperture;
a light emitter mounting member configured to receive a light emitter;
a channel;
a varus-valgus adjustment member configured to adjust a position of the positioning assembly relative to the femur to achieve a desired varus-valgus angle; and
a flexion-extension adjustment member configured to adjust a flexion-extension position of the positioning assembly; and
a guide member configured to extend from a depth selector slide, the depth selector slide configured to be received within the channel of the positioning assembly, wherein the light emitter mounting member includes a light emitter receiving aperture configured to receive at least a portion of the light emitter, further including a magnetic interface for magnetically securing the light emitter to the light emitter mounting member, and wherein the light emitter comprises a magnetic switch that is configured to be activated to power on the light emitter when received by the light emitter mounting member.

14. A bone cut positioning system, comprising:
a positioning assembly, including:
a femoral attachment member configured to be coupled to a distal end of a femur, including:
a base portion;
a first tongue portion having at least one fixation aperture configured to receive a fastening member, wherein the first tongue extends away from the base portion and is configured to be attached to the anterior cortex of the femur, thereby providing a flexion-extension axis reference; and
a second tongue portion having at least one fixation aperture configured to receive a fastening member, wherein the second tongue is configured to be attached to the distal end of the femur;
a light emitter mounting member configured to receive a light emitter;
a channel;
a magnetic interface disposed within the channel;
a varus-valgus adjustment member configured to adjust a position of the positioning assembly relative to the femur to achieve a desired varus-valgus angle; and
a flexion-extension adjustment member configured to adjust a flexion-extension position of the positioning assembly relative to a flexion-extension of a knee joint; and
a guide member extending from a depth selector slide, the depth selector slide configured to be received within the channel of the positioning assembly and secured within the channel by the magnetic interface.

15. A method for positioning a bone cut guide on a femur, comprising:
coupling a positioning assembly to a femur, the positioning assembly including;
a femoral attachment member, including a tongue with at least one fixation aperture configured to receive a pin;
a light emitter mounting member configured to receive a light emitter;
a channel;
a varus-valgus adjustment member configured to adjust a position of the positioning assembly relative to the femur to achieve a desired varus-valgus angle; and
a flexion-extension adjustment member configured to adjust a flexion-extension position of the positioning assembly relative to a flexion-extension of a knee joint;
attaching the light emitter to the light emitter mounting member, the light emitter configured to indicate a varus-valgus angle of the femur;
inserting a depth selector slide of a guide member into the channel;
aligning the guide member relative to a distal end surface of the femur;
coupling the guide member to the femur with at least one guide pin;
removing the positioning assembly and the guide member from the femur; and
sliding the bone cut guide over the at least one guide pin.

16. The method of claim 15, further including adjusting the varus-valgus adjustment member to align a position of the positioning assembly with the indicated varus-valgus angle of the femur.

17. The method of claim 15, further including adjusting the flexion-extension adjustment member to align a position of the positioning assembly with a flexion-extension angle of the knee joint.

18. The method of claim 15, wherein the method is performed on a leg in full extension.

19. The method of claim 15, further including adjusting the depth selector slide to a desired resection level.

* * * * *